US011324531B2

(12) United States Patent
Voic et al.

(10) Patent No.: US 11,324,531 B2
(45) Date of Patent: May 10, 2022

(54) ULTRASONIC SURGICAL DRILL, ASSEMBLY AND ASSOCIATED SURGICAL METHOD

(71) Applicant: MISONIX, INCORPORATED, Farmingdale, NY (US)

(72) Inventors: Dan Voic, Cedar Grove, NJ (US); Paul Mikus, Trabuco Canyon, CA (US)

(73) Assignee: MISONIX, INCORPORATED, Farmingdale, NY (US)

(*) Notice: Subject to any disclaimer, the term of this patent is extended or adjusted under 35 U.S.C. 154(b) by 369 days.

(21) Appl. No.: 16/388,512

(22) Filed: Apr. 18, 2019

(65) Prior Publication Data

US 2019/0321066 A1   Oct. 24, 2019

Related U.S. Application Data (60) Provisional application No. 62/660,625, filed on Apr. 20, 2018.

(51) Int. Cl.
*A61B 17/32* (2006.01)
*A61B 17/16* (2006.01)

(52) U.S. Cl.
CPC .. *A61B 17/320068* (2013.01); *A61B 17/1615* (2013.01); *A61B 17/1637* (2013.01); *A61B 17/1671* (2013.01); *A61B 2017/1651* (2013.01); *A61B 2017/320084* (2013.01)

(58) Field of Classification Search
CPC ............ A61B 17/1615; A61B 17/1622; A61B 17/1624; A61B 17/1626; A61B 17/1628; A61B 17/32002; A61B 17/320068; A61B 2017/320032; A61B 2017/320073; A61B 2017/32007; A61B 2017/320078
See application file for complete search history.

(56) References Cited

U.S. PATENT DOCUMENTS

| 5,176,677 | A  | * | 1/1993  | Wuchinich | ................ | A61F 2/46 606/46 |
| 6,352,532 | B1 | * | 3/2002  | Kramer    | .......... | A61B 17/320092 606/41 |
| 7,431,704 | B2 | * | 10/2008 | Babaev    | .......... | A61B 17/320068 601/2 |
| 8,025,672 | B2 | * | 9/2011  | Novak     | ............. | A61B 17/22004 606/169 |
| 9,226,767 | B2 | * | 1/2016  | Stulen    | ................ | A61B 18/1445 |

(Continued)

FOREIGN PATENT DOCUMENTS

| WO | WO 2009/098664 A2 | 8/2009 |
| WO | WO 2009/105628 A2 | 8/2009 |

*Primary Examiner* — Anu Ramana
(74) *Attorney, Agent, or Firm* — R. Neil Sudol; Henry D. Coleman (57) ABSTRACT

A medical drill assembly includes a probe connectable at a proximal end to an electromechanical transducer for generating mechanical vibration of an ultrasonic frequency. The probe has a shaft with a central lumen or channel, the shaft being formed at a distal end with a head having a tapered distal side. A source of pressurized liquid communicates with the lumen or channel of the probe, and a translatory or linear drive is operatively connected to the probe for applying a distally directed force to the probe. A controller is operatively connected to the translatory or linear drive for periodically at least reducing the magnitude of the distally directed force.

16 Claims, 6 Drawing Sheets

(56) References Cited

U.S. PATENT DOCUMENTS

| | | |
|---|---|---|
| 9,320,528 B2 | 4/2016 | Voic et al. |
| 9,962,182 B2 * | 5/2018 | Dietz .............. A61B 17/320068 |
| 2008/0015551 A1 * | 1/2008 | Feine ............. A61B 17/320068 |
| | | 606/1 |
| 2008/0057470 A1 * | 3/2008 | Levy ...................... A61C 19/00 |
| | | 433/118 |
| 2008/0058648 A1 * | 3/2008 | Novak ............. A61B 17/22004 |
| | | 600/471 |
| 2008/0058775 A1 * | 3/2008 | Darian ........... A61B 17/320068 |
| | | 606/1 |
| 2008/0183173 A1 | 7/2008 | Jozat |
| 2010/0022944 A1 * | 1/2010 | Wilcox .............. A61B 17/2202 |
| | | 604/22 |
| 2013/0123774 A1 * | 5/2013 | Zadeh ................... A61B 17/16 |
| | | 606/39 |
| 2015/0005775 A1 | 1/2015 | Voic |
| 2015/0164534 A1 * | 6/2015 | Felder ........... A61B 17/320092 |
| | | 606/169 |
| 2015/0297246 A1 * | 10/2015 | Patel ................. A61B 17/3478 |
| | | 606/79 |
| 2016/0175150 A1 * | 6/2016 | Banko ................ A61F 9/00745 |
| | | 606/171 |

\* cited by examiner

FIG. 10

ULTRASONIC SURGICAL DRILL, ASSEMBLY AND ASSOCIATED SURGICAL METHOD

FIELD OF THE INVENTION

This invention relates to an ultrasonic bone drill. This invention also relates to an ultrasonic surgical drilling assembly. The method also relates to an associated method.

BACKGROUND OF THE INVENTION

In the field of orthopedics, the cutting of living bone is a prerequisite for many procedures. Such procedures include the reconstruction of damaged tissue structures due to accidents, the grafting of healthy bone into areas damaged by disease, or the correction of congenital facial abnormalities like a receding chin line. Over several centuries, these tasks were performed through the utilization of devices called bone saws.

Traditional bone saws are categorized into several basic categories. Hand powered saws or drills are just that, hand held devices which require the operator to move the device in a fashion similar to that used for carpentry tools. Powered devices, whether electric or pneumatic, are of either the reciprocating or rotary type. The reciprocating devices use a flat, sword like blade where the back and forth motion is provided by a motor instead of the hand. The rotary devices use a rotating motor to spin a drill bit or a blade which has teeth arranged around its circumference similar to a table saw blade. All of these traditional bone saws are used today in medical procedures around the world.

There are many spinal operations where it is necessary to cut into or perforate hard bone. Decompression of the spinal canal requires removal or bone or disc. In order to stabilize the spinal column the adjacent levels are fused. This requires hardware such as screws and rods. Prior to installing the screws, the surgeon needs to drill holes of a diameter smaller than that of the screws. Since the bone is very hard, it is necessary to apply significant pressure to drill the holes.

In the past, surgeons have used hand braces and bits of a design very similar to those used for non-medical purposes, for example carpentry. Such tools are not completely satisfactory because it has been found that such tools can cut through the bone and damage the nerves of the spinal cord.

It has been found that ultrasonic blades, if properly designed and properly used, can cut bone without damaging the soft tissue adjacent the bone. U.S. Patent Application Publication No. 20050273127 by Novak et al. discloses a surgical blade and a related method of use of that surgical blade in an ultrasonically assisted procedure for cutting bone, wherein adjacent soft tissue is not damaged. The observation was made that the sharper the blade, i.e., the smaller the minor dimension of a vertical trapezoid formed by the included angle of a blade of width N, the more likely that cutting of hard tissues resulted in collateral damage, particularly incisions, in surrounding soft tissue. It was discovered that blades with an edge thickness between approximately 0.001" and approximately 0.010" inch offered the best compromise between effective, safe cutting of hard tissue such as bone while being sparing of surrounding soft tissue.

The teachings of U.S. Patent Application Publication No. 20050273127 pertain to linear cutting blades moved by a reciprocating sawing-type motion, and not to rotary tools.

Drilling into bone evidently requires its own protective technique and associated tool for minimizing or avoiding damage to brain tissues.

SUMMARY OF THE INVENTION

The present invention aims to provide an improved ultrasonic drill, particularly with an improved ultrasonic drill bit or head, that is especially configured for drilling into bone such as a skull.

A medical drill assembly comprises, in accordance with the present invention, a probe connectable at a proximal end to an electromechanical transducer for generating mechanical vibration of an ultrasonic frequency. The probe has a shaft with a central lumen or channel, the shaft being formed at a distal end with a head having a tapered distal side. The assembly further comprises a source of pressurized liquid communicating with the lumen or channel, a translatory or linear drive operatively connected to the probe for applying a distally directed force to the probe, and a controller operatively connected to the translatory or linear drive for periodically at least reducing the magnitude of the distally directed force.

Pursuant to another feature of the invention the distal side of the head is provided with at least one port or opening communicating with the lumen or channel.

Preferably, the distal side of the head is formed with a plurality of force-concentrating formations. The force-concentrating formations are exemplarily taken from the groups comprising knurls, beads, and teeth. It is contemplated that the distal side of the head is covered throughout with the force-concentrating formations.

The at least one port or opening may be centrally located in the distal side of the head. Where the port or opening is one of a plurality or ports or openings in the distal side of the head, all of the ports or openings communicate with the lumen or channel.

The translatory or linear drive may reversible, in which case the controller is operatively connected to the translatory or linear drive to periodically reverse the translatory or linear drive, thereby reducing the magnitude of the distally directed force to zero for intervals of time.

Pursuant to another feature of the present invention, the controller is operatively connected to the electromechanical transducer for energizing same with an electrical waveform having the ultrasonic frequency and for pulsing the frequency so that the mechanical vibration is periodically interrupted for a predetermined period of time. Where the interruption or reduction of the distally directed force has a given frequency or period, the pulsing of the ultrasonic vibratory preferably has a frequency that is greater than the frequency of interruption or reduction in the application of force to the probe. (One might consider, then that at least three frequencies are involved in controlling the probe during an operation: the frequency of ultrasonic vibration, the frequency of pulsing the ultrasonic vibratory energy, and the frequency of interruption of the force of application.)

Pursuant to a feature of the present invention, the distal side of the probe head has a geometric form that is axially symmetric. Preferably, the distal side has a shape that is conical, frusto-conical, convex, or concave. In a convex case, the slope of the distal side of the probe head, or of an envelope thereof, is greatest at the proximal end of the probe head and decreases in a distal direction to be least at the distal end of the probe. In the concave case, the opposite occurs, that is, the slope of the distal side of the probe head, or of an envelope thereof, is least at the proximal end of the probe head and increases in a distal direction to have a greatest value at the distal end. The slope may be measured with the probe in a vertical orientation, with a vertical y-axis and a horizontal x-axis.

It is to be noted further that the distal side of the probe head may have some variation in the shape. For instance, the distal side may a combination or mixture of different tapering shapes, such as an assemblage of convex, concave, and conical. More specifically, a distal most end portion of the heads distal side may be conical while a more proximal portion is convex or concave.

A surgical method pursuant to the present invention utilizes an ultrasonic probe having a shaft with a central lumen or channel, the shaft being formed at a distal end with an enlarged head tapering down on a distal side, the lumen or channel terminating in a port or opening at an outer surface of the head. The method comprises connecting the probe at a proximal end to a source of ultrasonic vibratory energy, connecting the lumen or channel to a source of pressurized liquid, coupling the probe to a mechanical drive, pacing the distal side of the probe head against a surface of a bone, and while the distal side is in contact with the bone surface, operating the transducer to vibrate the head and the distal side at an ultrasonic frequency. While the distal side of the head is in contact with the surface of the bone and during the operating of the transducer, one actuates the drive to exert a force on the probe tending to push the probe into the bone and conducts liquid through the lumen or channel to the port or opening. While the distal side is in contact with the surface of the bone and while the liquid is being conducted through the lumen or channel to the port or opening, the actuating of the drive is periodically interrupted so as to reduce, if not eliminate, the distally directed force. Elimination of the force occurs when the drive is reversed to pull the probe in a proximal direction, away from the bone tissue.

DETAILED DESCRIPTION

Figure 1:
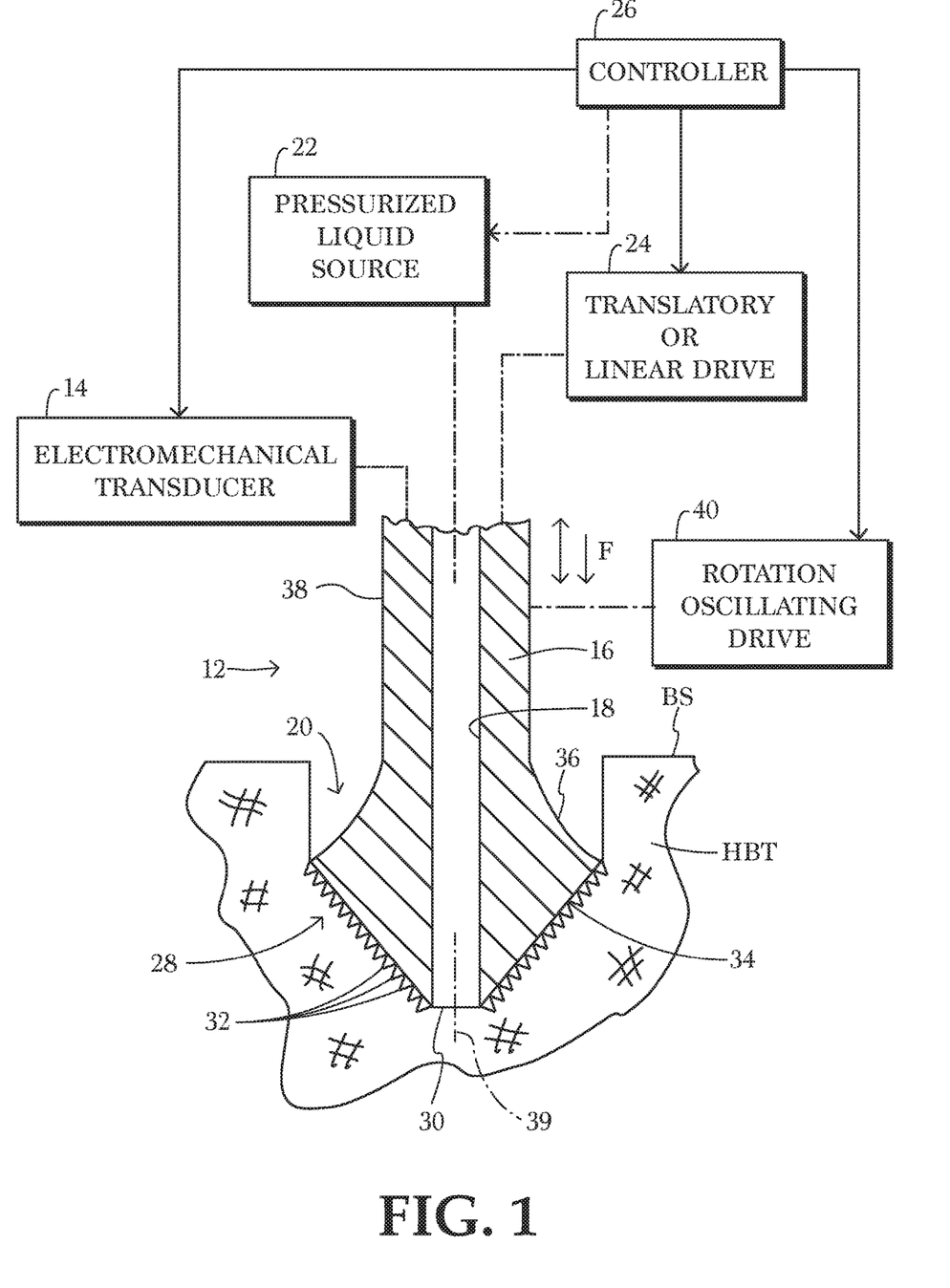
FIG. 1 is partially a block diagram and partially a schematic partial longitudinal cross-sectional view of a probe of a surgical treatment assembly in accordance with the present invention.

As depicted in FIG. 1, a medical drill assembly particularly for drilling holes into bone that is not previously perforated comprises a probe 12 connectable at a proximal end to an electromechanical transducer 14 for generating mechanical vibration of an ultrasonic frequency, typically between 22 KHz and 1 MHz. The transducer is typically a piezoelectric element or stack of such elements, or may alternatively be of a magnetostrictive type. Probe 12 has a shaft 16 with a central lumen or channel 18 and is formed at a distal end with an enlarged conical or frusto-conical head 20. A source 22 of pressurized liquid such as saline solution communicates with lumen of channel 18. Source 22 may be realized a peristaltic pump or other pumping mechanism.

A translatory or linear drive 24 is operatively connected to probe 12 for applying a distally directed force F to the probe. In the case that probe 12 is manually held, drive 24 assists in pressing probe head 20 through a bone surface BS and into hard bone tissue HBT. In the case of a robotically mounted probe 12, drive 24 may be responsible for supporting the probe and moving the probe into contact with target bone tissue HBT.

A controller 26 is operatively connected to the translatory or linear drive 24 for activating the drive and periodically at least reducing the magnitude of the distally directed force F during a surgical bone drilling procedure. Reduction may be accomplished by reversing drive 24, so that probe 12 is temporarily withdrawn or retracted from its most distal location inside the bone at the surgical site.

The reduction in, or reversal of, force F typically occurs with a periodicity ranging from a tenth of a second to one or two seconds. The interruption generally has a duration on the order of a fraction of a second (e.g., 0.1 second to 1 second). The interruption in the application of force F, whether a reduction in pressure or a reversal of the probe's direction of motion, enables the pressurized liquid from source 22 to clear osseous debris from central lumen or channel 18, thereby ensuring continued delivery of coolant to the surgical site and removal of debris.

Controller 26 typically includes a computer or processor (e.g., 712, FIG. 10) and a waveform generator (710, FIG. 10) that is preferably digital as described in U.S. Pat. Nos. 8,659,208 and 9,070,856, the disclosures of which are hereby incorporated by reference. Controller 26 preferably continues to energize transducer 14 during all or a portion of the time that force F is interrupted or probe 12 is retracted, which serves to facilitate the dislodging and ejection of debris from lumen or channel 18. Probe 12 is preferably provided with an ancillary port in shaft 16 or a proximal portion of head 20 that communicates with lumen or channel 18 to release excess liquid pressure.

A rotary or oscillating drive 40 may be operatively connected to probe 12 for applying a sector rotation to the probe. Drive 40 oscillates probe 12 about a longitudinal axis 39 of probe 12 through an angle of up to 45° in each angular direction, clockwise and counterclockwise, from a rest position. This oscillating sector rotation may be applied during the application of longitudinal force F by drive 24 and may be continued, reduced or stopped during the interruption, reduction or reversal of force F.

Probe head 20 has a distal side 28 that is conically shaped and provided with at least one port or opening 30 communicating with lumen or channel 18. Distal side 28 of probe head 20 is formed with a plurality of force-concentrating formations 32 that are pyramidal knurls, beads, or teeth. Preferably a conical portion 34 of distal head side 28 is covered throughout with the force-concentrating formations 32.

Distal side 28 of probe head 20 takes the form of a truncated cone, with port or opening 30 at the center, in the truncated area of the cone. Probe head 20 has a proximal axially symmetric surface 36 which is tapered in a curve of changing slope towards an outer surface 38 of shaft 14.

Figure 2A:
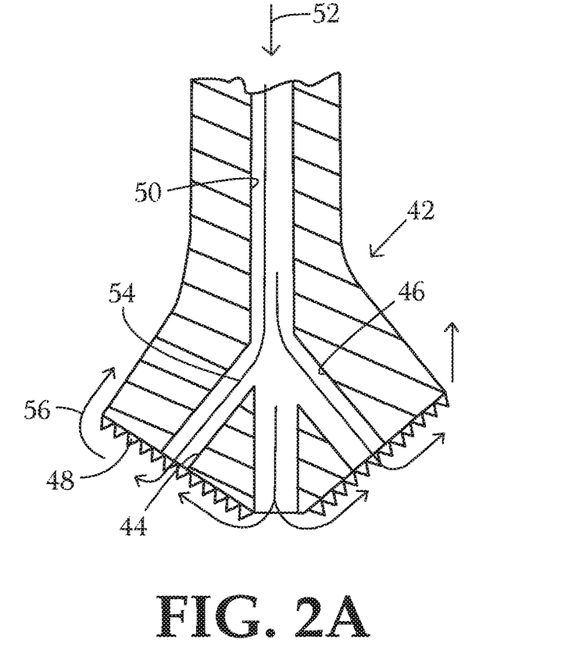
FIG. 2A is a schematic partial longitudinal cross-sectional view of a modification of the probe of FIG. 1.

FIG. 2A shows a modified probe head 42, utilizable as part of probe 12 in the system or assembly of FIG. 1, that is provided with a plurality of ducts or branching channels 44, 46 that extend to a conical distal side 48 of the probe head from a central lumen or channel 50 that performs the same irrigation function as lumen or channel 18 in FIG. 1. The irrigant is used to cool the probe head, particularly along the tissue-prove interface. Arrows 52, 54, 56 show the flow path of liquid irrigant during a surgical procedure.

Figure 2B:
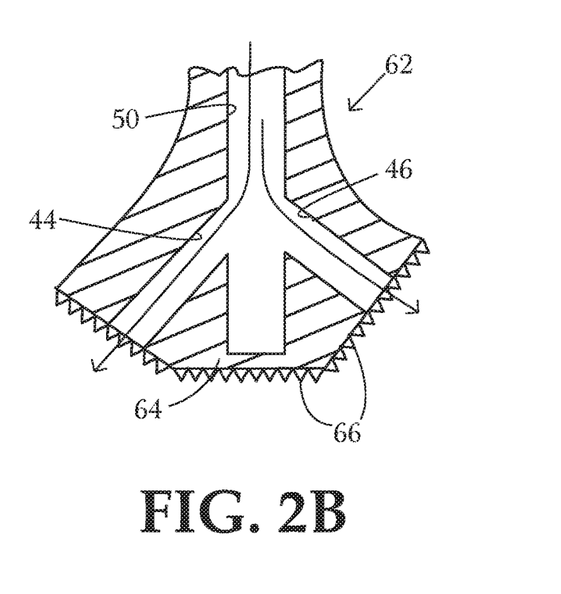
FIG. 2B is a schematic partial longitudinal cross-sectional view of another modification of the probe of FIG. 1.

FIG. 2B shows another modified probe head 62, utilizable as part of probe 12 in the system or assembly of FIG. 1, where the central channel is closed or blocked at 64. Teeth 66 can extend across the truncated end. The advantage of this embodiment is that it helps with preventing a forward shooting jet of irrigant from reaching unintended tissue as when the port or opening 30 is full size.

Figure 3A:
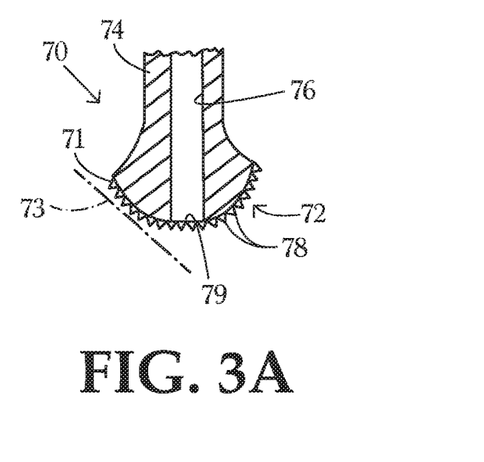
FIG. 3A is a schematic partial longitudinal cross-sectional view of a different modification of the probe of FIG. 1.

As illustrated in FIG. 3A, a probe head 70 utilizable as part of probe 12 in the system or assembly of FIG. 1 has a distal side 72 with a shape that is convex rather than conical or frusto-conical. A probe incorporating head 70 has a shaft 74, a lumen or channel 76 for liquid irrigant conduction, and a layer of force-concentrating formations 78 such as pyramidal beads or teeth. Lumen or channel 76 terminates in a port or opening 79 at a distal tip (not separately designated) of the instrument. Distal side 70, or an envelope thereof, has a slope that is greatest at the proximal end 71 of the probe head 70 and decreases in a distal direction to be least at the distal end of the probe. A slope line 73 becomes increasingly horizontal as one proceeds in the distal direction from proximal end 71.

Figure 3B:
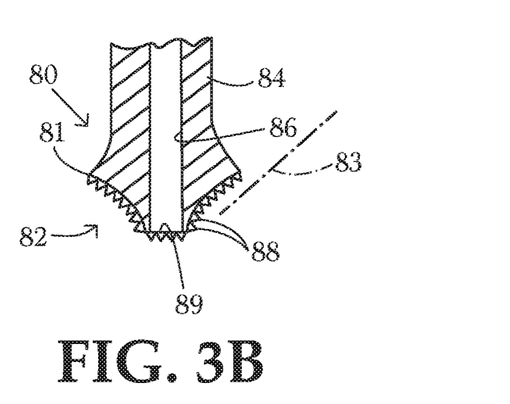
FIG. 3B is a schematic partial longitudinal cross-sectional view of yet another modification of the probe of FIG. 1.

FIG. 3B shows a probe head 80, utilizable as part of probe 12 in the system or assembly of FIG. 1, has a distal side 82 with a shape that is concave rather than conical or frusto-conical. A probe incorporating head 80 has a shaft 84, a lumen or channel 86 for liquid irrigant conduction, and a layer of force-concentrating formations 88 such as pyramidal beads or teeth. Lumen or channel 86 terminates in a port or opening 89 at a distal tip (not separately designated) of the instrument. Distal side 80, or an envelope thereof, has a slope that is least at the proximal end 81 of the probe head 80 and increases in a distal direction to be least at the distal end of the probe. A slope line 83 becomes increasingly vertical as one proceeds in the distal direction from proximal end 81.

FIGS. 4 and 5A-5D show a probe 112 with a shaft 116 having a central axial lumen or channel 118 and a head 120. Head 120 includes a tapered distal side portion 122, a central cylindrical portion 124 and a proximal tapered portion 126. Distal and proximal tapered portions 122 and 126 are formed with force-concentrating pyramidal teeth 128 and 130, while center cylindrical portion 124 is smooth. Head 120 is connected to a cylindrical portion 132 of shaft 116 via a slight tapered region 134. At a predetermined distance from head 112, depending on the expected depth of drill holes to be formed in bone tissue during surgical procedure, shaft 116 may exhibit a gently or gradually shaped portion or horn section 136 which serves to increase the amplitude of longitudinal vibration.

Figure 4:
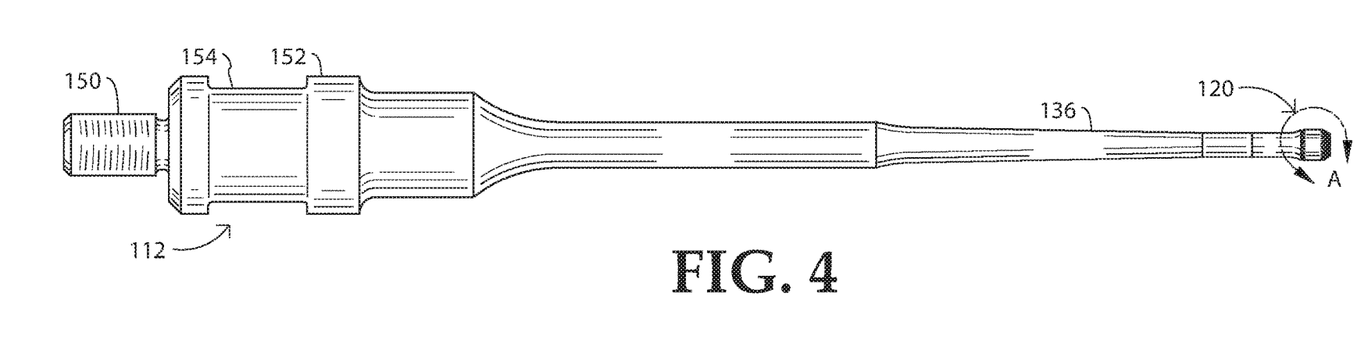
FIG. 4 is a side elevational view of a probe in accordance with the present invention.
Figure 5A:
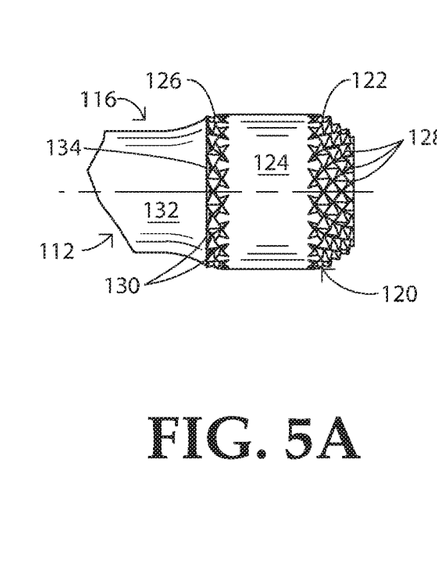
FIG. 5A is a side elevational view, on an enlarged scale, of the distal end of the probe of FIG. 4.
Figures 5B, 5C:
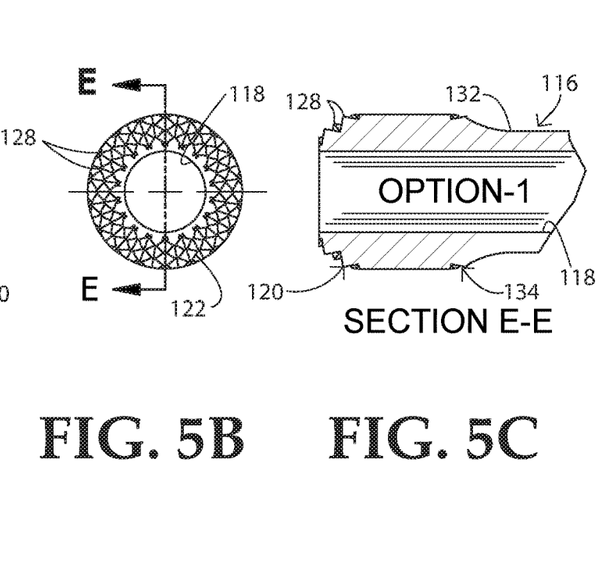
FIG. 5B is a distal end elevational view of the probe of FIGS. 4 and 5A.
FIG. 5C is a longitudinal cross-sectional view, on an enlarged scale, of the distal end of the probe of FIG. 4, taken along line E-E in FIG. 5B.
Figure 5D:
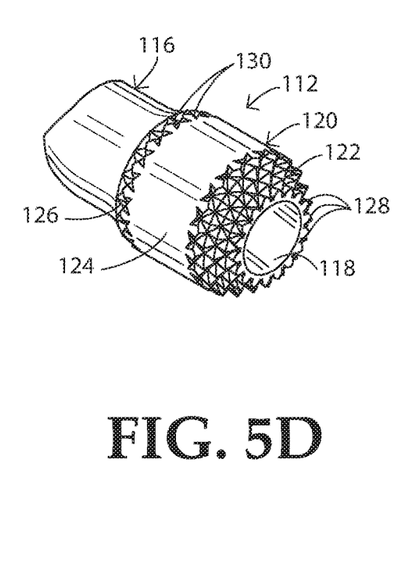
FIG. 5D is an isometric view, on an enlarged scale, of the distal end of the probe of FIG. 4.
Figure 6A:
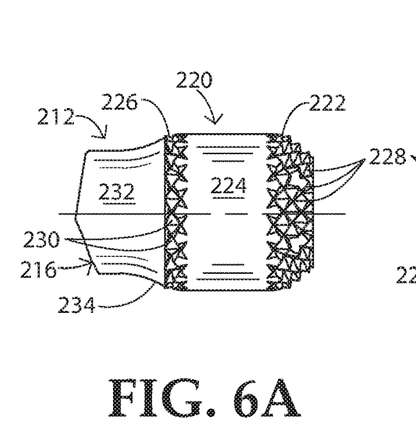
FIG. 6A is a side elevational view, on an enlarged scale, of a first modification of the distal end of the probe of FIG. 4.
Figures 6B, 6C:
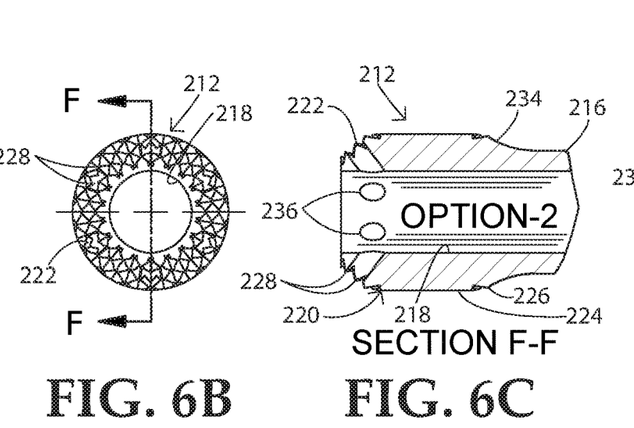
FIG. 6B is a distal end elevational view, on an enlarged scale, of the modified probe end of FIG. 6A.
FIG. 6C is a longitudinal cross-sectional view, on an enlarged scale, of the modified probe end of FIGS. 6A and 6B, taken along line F-F in FIG. 6B.
Figure 6D:
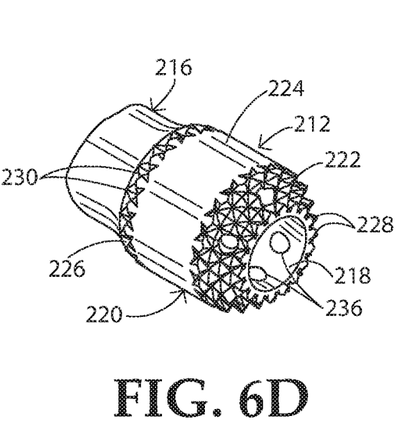
FIG. 6D is an isometric view, on an enlarged scale, of the modified probe end of FIGS. 6A through 6C.
Figure 7A:
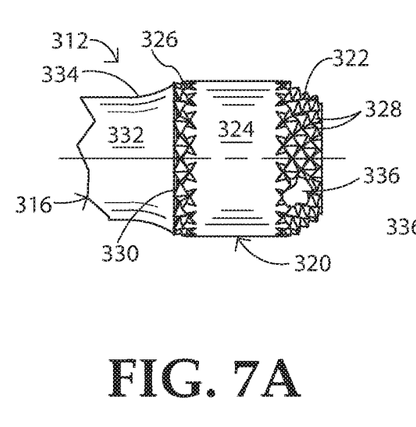
FIG. 7A is a side elevational view, on an enlarged scale, of a second modification of the distal end of the probe of FIG. 4.
Figures 7B, 7C, 7D:
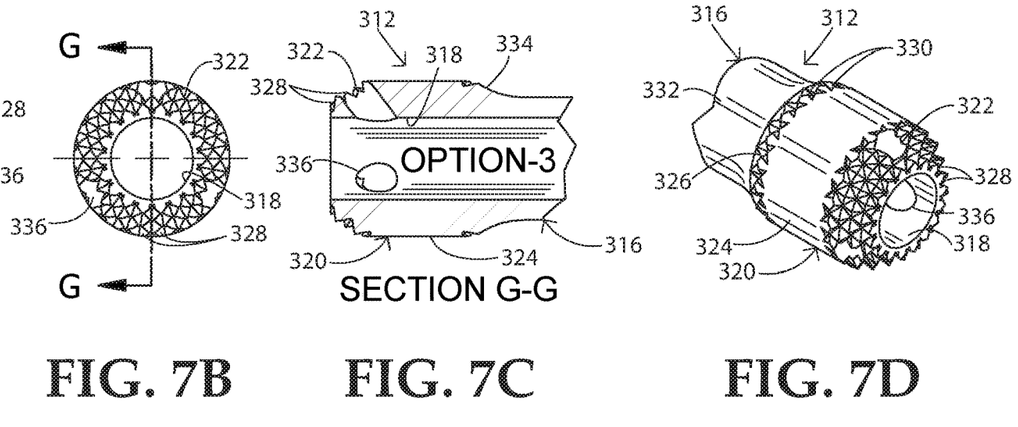
FIG. 7B is a distal end elevational view, on an enlarged scale, of the modified probe end of FIG. 7A.
FIG. 7C is a longitudinal cross-sectional view, on an enlarged scale, of the modified probe end of FIGS. 7A and 7B, taken along line G-G in FIG. 7B.
FIG. 7D is an isometric view, on an enlarged scale, of the modified probe end of FIGS. 7A through 7C.
Figures 8A, 8B:
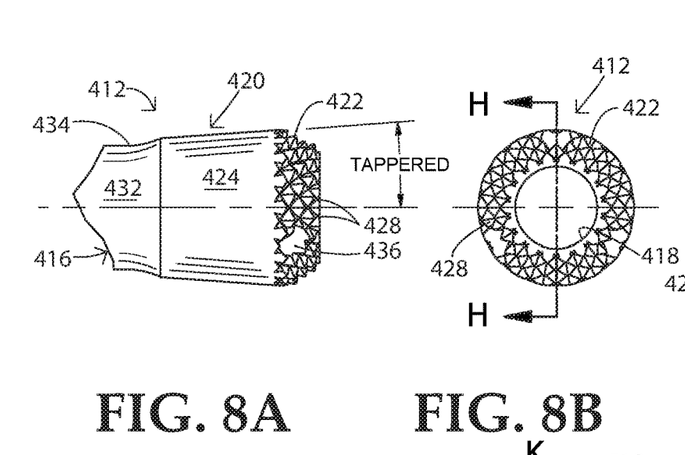
FIG. 8A is a side elevational view, on an enlarged scale, of a third modification of the distal end of the probe of FIG. 4.
FIG. 8B is a distal end elevational view, on an enlarged scale, of the modified probe end of FIG. 8A.
Figure 8C:
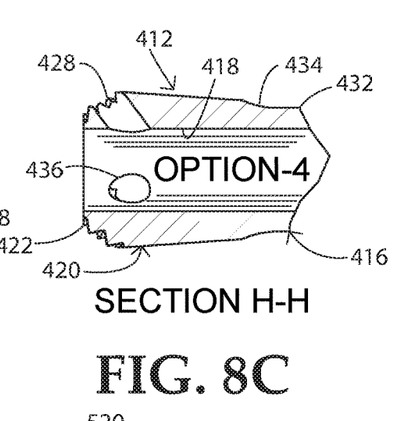
FIG. 8C is a longitudinal cross-sectional view, on an enlarged scale, of the modified probe end of FIGS. 8A and 8B, taken along line H-H in FIG. 9B.
Figures 8D, 9D:
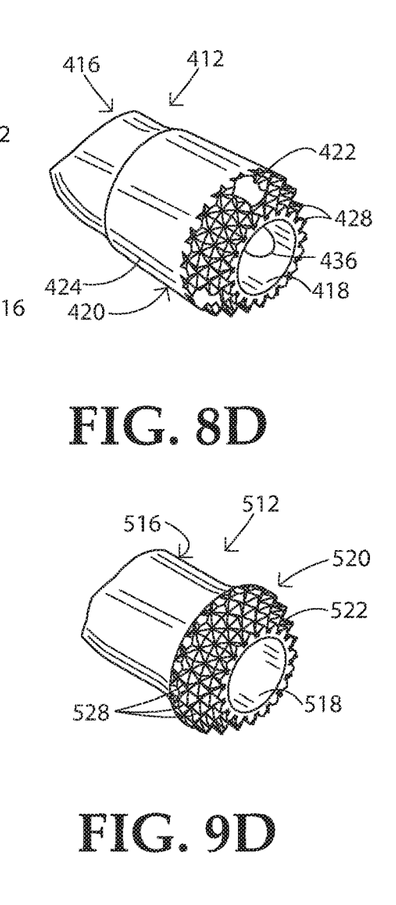
FIG. 8D is an isometric view, on an enlarged scale, of the modified probe end of FIGS. 8A through 8C.
FIG. 9D is an isometric view, on an enlarged scale, of the modified probe end of FIGS. 9A through 9C.
Figure 9A:
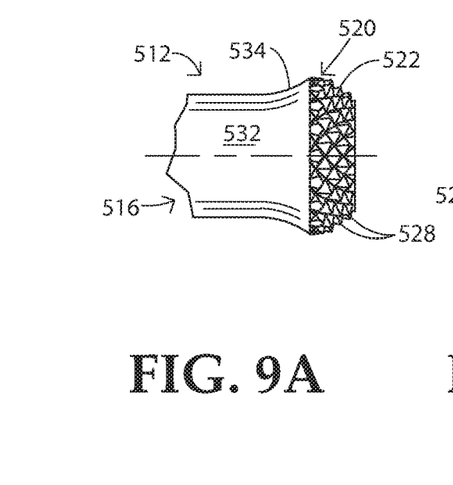
FIG. 9A is a side elevational view, on an enlarged scale, of a second modification of the distal end of the probe of FIG. 4.
Figure 9B:
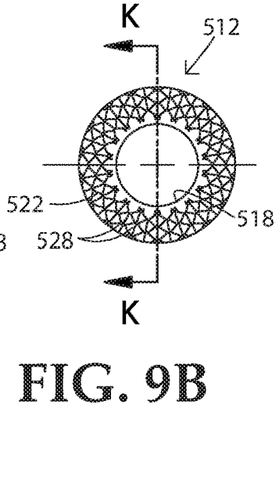
FIG. 9B is a distal end elevational view, on an enlarged scale, of the modified probe end of FIG. 9A.
Figure 9C:
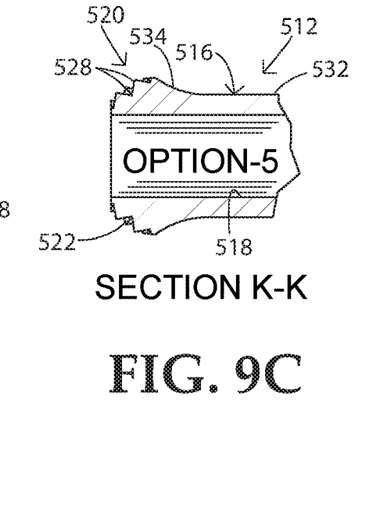
FIG. 9C is a longitudinal cross-sectional view, on an enlarged scale, of the modified probe end of FIGS. 9A and 9B, taken along line K— in FIG. 9B.

Probe 112 is provided at a proximal end with a threaded connector 150 for connecting the probe to an electromechanical transducer 14 (FIG. 1) and a proximal portion 152 with flats 154 for tightening the coupling of probe 112 to the transducer 14 with a wrench.

FIGS. 6A-6D show a probe 212 with a shaft 216 having a central axial lumen or channel 218 and a head 220. Head 220 includes a conically tapered distal side portion 222, a central cylindrical portion 224 and a proximal tapered portion 226. Distal and proximal tapered portions 222 and 226 are formed with force-concentrating pyramidal teeth 228 and 230, while center cylindrical portion 224 is smooth. Head 220 is connected to a cylindrical portion 232 of shaft 216 via a short tapered region 234. At a predetermined distance from head 212, depending on the expected depth of drill holes to be formed in bone tissue during surgical procedure, shaft 216 may exhibit a gently or gradually shaped portion or horn section which serves to increase the amplitude of longitudinal vibration. Head 220 is provided with ancillary ducts 236 that branch from central lumen or channel 218 and extend to distal tapered portion 222.

FIGS. 7A-7D show a probe 312 with a shaft 316 having a central axial lumen or channel 318 and a head 320. Head 320 includes a conically tapered distal side portion 322, a central cylindrical portion 324 and a proximal tapered portion 326. Distal and proximal tapered portions 322 and 326 are formed with force-concentrating pyramidal teeth 328 and 330, while center cylindrical portion 324 is smooth. Head 320 is connected to a cylindrical portion 332 of shaft 216 via a short tapered region 334. At a predetermined distance from head 312, depending on the expected depth of drill holes to be formed in bone tissue during surgical procedure, shaft 316 may exhibit a gently or gradually shaped portion or horn section which serves to increase the amplitude of longitudinal vibration. Head 320 is provided with ancillary ducts 336, larger than ducts 236, that branch from central lumen or channel 318 and extend to distal tapered portion 322.

FIGS. 8A-8D show a probe 412 with a shaft 416 having a central axial lumen or channel 418 and a head 420. Head 420 includes a conically tapered distal side portion 422 and a main portion 424. Distal tapered portion 422 is formed with force-concentrating pyramidal teeth 428, while main portion 424 is smooth. This main portion 424 exhibits a decrease in diameter, that is, a tapering down, in a proximal direction. Head 420 is connected to a cylindrical portion 432 of shaft 416 via a short tapered region 434. At a predetermined distance from head 412, depending on the expected depth of drill holes to be formed in bone tissue during surgical procedure, shaft 416 may exhibit a gently or gradually shaped portion or horn section which serves to increase the amplitude of longitudinal vibration. Head 420 is provided with ancillary ducts 436, similar to ducts 336, that branch from central lumen or channel 418 and extend to distal tapered portion 422.

FIGS. 9A-9D show a probe 512 with a shaft 516 having a central axial lumen or channel 518 and a head 520. Head 520 includes a conically tapered distal side portion 522 formed with force-concentrating pyramidal teeth 528. On a proximal side, opposite conically tapered portion 528, head 520 is connected to a cylindrical portion 532 of shaft 516 via a short tapered region 534. At a predetermined distance from head 512, depending on the expected depth of drill holes to be formed in bone tissue during surgical procedure, shaft 516 may exhibit a gently or gradually shaped portion or horn section which serves to increase the amplitude of longitudinal vibration. Head 520 may be optionally provided with ancillary ducts, similar to ducts 236 or 336, that branch from central lumen or channel 518 and extend to distal tapered portion 522.

All of the above-described probes may be utilized in the medical or surgical assembly of FIG. 1, in substitution for probe 12.

At least one port or opening is one of a plurality or ports or openings in the distal side of the head, all of the ports or openings communicating with the lumen or channel.

It is to be noted that drive 24 may be reversible, controller 26 being operatively connected to drive 24 to periodically reduce the magnitude of force F to zero and to even withdraw the probe 12, 112, 212, 312, 412, 512 slightly before re-instituting the application of distally directed force F.

Preferably, during the periods where controller 26 causes drive 24 to reduce, if not entirely cease, the application of distally directed force F to probe 12, 112, 212, 312, 412, 512, electromechanical transducer 14 continues to generate ultrasonic-frequency vibrations in the probe. This results in a shaking loose and disruption of tissue that may be adhering to the distal side 28 of the probe 12, 112, 212, 312, 412, 512, lodged for instance in between teeth or knurls 32, 128, 228, 328, 428, 528. Controller 26 is operatively connected to transducer 14 for energizing same with an electrical waveform having the ultrasonic frequency and may be configured for pulsing the ultrasonic waveform or frequency so that the ultrasonic vibration of the probe 12, 112, 212, 312, 412, 512 and its head 20, 120, 220, 320, 420, 520 is periodically interrupted for a predetermined period of time. Where the periodic reduction of the magnitude of the distally directed force F has a predetermined frequency or periodicity, the pulsing of the ultrasonic energization waveform or frequency has a pulsation frequency or rate that is greater than the predetermined frequency or periodicity of reduction of force F by drive 24.

Pulsation of the ultrasonic waveform or frequency exemplarily occurs with a duty cycle of between 80% and 90%. Thus, with a period of 250 msec, the off portion of the ultrasonic vibratory energy would have a duration of 25 to 50 msec.

In another mode of operation of the surgical treatment assembly of FIG. 1, controller 26 may activate drive 24 to continually press the probe 12, 112, 212, 312, 412, 512 into the bone tissue I-IBT during the entire procedure. The ultrasonic transducer 14 may be energized continuously or in pulsed mode.

The assembly of FIG. 1 is able to effectively cool the instrument and prevent excessive heat application to the bone tissue owing to the flow of liquid through distal end port or opening 30 (and/or via branches or ducts 44 and 46). When the probe 12, 112, 212, 312, 412, 512 is driven into tissue HBT by drive 24, the backup pressure resulting from the flow restriction created by the probe-tissue contact helps with maintaining sufficient flow to prevent tissue heating. The potential for tissue heating is further reduced when the driving force is stopped and/or reversed for a brief interval. During this time, the wetting of the probe distal end 28, 122, 222, 322, 422, 522 is more efficient, improving the removal of heat. The constant presence of liquid at the instrument-tissue interface improves cavitational effects and tissue penetration efficiency. When force F is interrupted, whether drive merely eases off or reverses, the ultrasonic vibration is preferably maintained. This ensures that any tissue temporarily retained by the probe geometry is released.

It is to be noted that the ultrasonic vibratory motion of probe 12, 112, 212, 312, 412, 512 may be longitudinal, torsional or a combination of these two vibration modes.

In a surgical method utilizing the assembly of FIG. 1 with any probe 12, 112, 212, 312, 412, 512 and especially the last two, it is observed that the probe head is an enlarged head that tapers down in a distal direction to a tip or apex, which may be blunted by the presence of an irrigant outlet port or opening 30, 79, 89. The method contemplates connecting the probe 12, 112, 212, 312, 412, 512 at a proximal end to a source of ultrasonic vibratory energy, connecting the lumen or channel 18, 118, 218, 318, 418, 518 to a source 22 of pressurized liquid, and coupling the probe 12, 112, 212, 312, 412, 512 to a mechanical drive. The method further includes placing the tip or distal side 28, 72, 82, 122, 222, 322, 42, 522 of the probe head 20, 70, 80, 120, 220, 320, 420, 520 against a surface BS of a bone and, while the tip or distal side 28, 72, 82, 122, 2222, 322, 422, 522 is in contact with the bone surface BS, operating transducer 14 to vibrate the head and the distal surface or side at an ultrasonic frequency. While the distal side 28, 72, 82, 122, 222, 322, 422, 522 is in contact with the surface of the bone and while operating the transducer 14, actuating the drive 24 to exert a force on the probe 12, 112, 212, 312, 412, 512 tending to push the probe into the bone. While the distal side of the head 20, 70, 80, 120, 220, 320, 420, 520 is in contact with the surface of the bone and while operating the transducer 14 to generate ultrasonic vibration (particularly a standing wave) in the probe, liquid is conducted through the lumen or channel 18, 76, 86, 118, 218, 318, 418, 518 to the port or opening 30, 79, 89 (or via channels 44, 46). Also, while the distal probe side 28, 72, 82, 122, 222, 322, 422, 522 is in contact with the surface of the bone BS and while the liquid is being conducted through the lumen or channel 18, 76, 86, 118, 218, 318, 418, 518 to the port or opening 30, 79, 89 (44, 46), one periodically interrupts the actuating of the drive 24 so as to reduce the force applied.

The periodic interrupting of actuating the drive 14 may include reversing the drive temporarily. "Interruption" or "interrupting" as that term us used herein, means that the pressure or force F acting to push the probe 12, 112, 212, 312, 412, 512 and its head 20, 70, 80, 120, 220, 320, 420, 520 into the bone HBT is at least reduced and possibly eliminated altogether, as when the operation of drive 14 is reversed. One may continue to operate the transducer 14 to vibrate the head 20, 70, 80, 120, 220, 320, 420, 520 and the distal head side 28, 72, 82, 122, 222, 322, 422, 522 while the actuating of the drive 24 is interrupted.

It is to be noted that the enlarged head 20, 70, 80, 120, 220, 320, 420, 520 of a probe 12, 112, 212, 312, 412, 512 as disclosed herein means that the drill hole is wider than the probe shaft 12, 74, 84, 116, 216, 316, 416, 516 which spaces the probe shaft from the tissue during the drilling of a deep hole, thereby reducing inadvertent damage to the tissue that would result from the probe shaft 12, 74, 84, 116, 216, 316, 416, 516 touching the wall of the drill hole. A deep hole may be required, for instance, in spinal reconstruction or reinforcement, as in disk fusions.

A sheath (not shown) may be provided about the shaft 12, 74, 84, 116, 216, 316, 416, 516 of the probe. The sheath may be passively retractable or spring loaded.

Various features disclosed herein in different embodiments, as depicted in the drawings, may be combined to form alternative embodiments. For instance, the embodiments of FIGS. 3A and 3B may be modified to incorporate the duct structure of FIG. 2A or FIG. 2B.

The distal sides of the probe head configurations disclosed herein are typically axially symmetric. However, it is within the scope of the invention that asymmetries may be included.

It is to be noted further that the distal side of the probe head may have some variation in the shape. For instance, the distal side may a combination or mixture of different tapering shapes, such as an assemblage of convex, concave, and conical. More specifically, a distal most end portion of the heads distal side may be conical while a more proximal portion is convex or concave.

The present invention may be used with bone-cutting probes other than surgical drills, for instance the blade disclosed in U.S. Pat. Nos. 6,379,371, 6,443,969 and 9,387,005.

Figure 10:
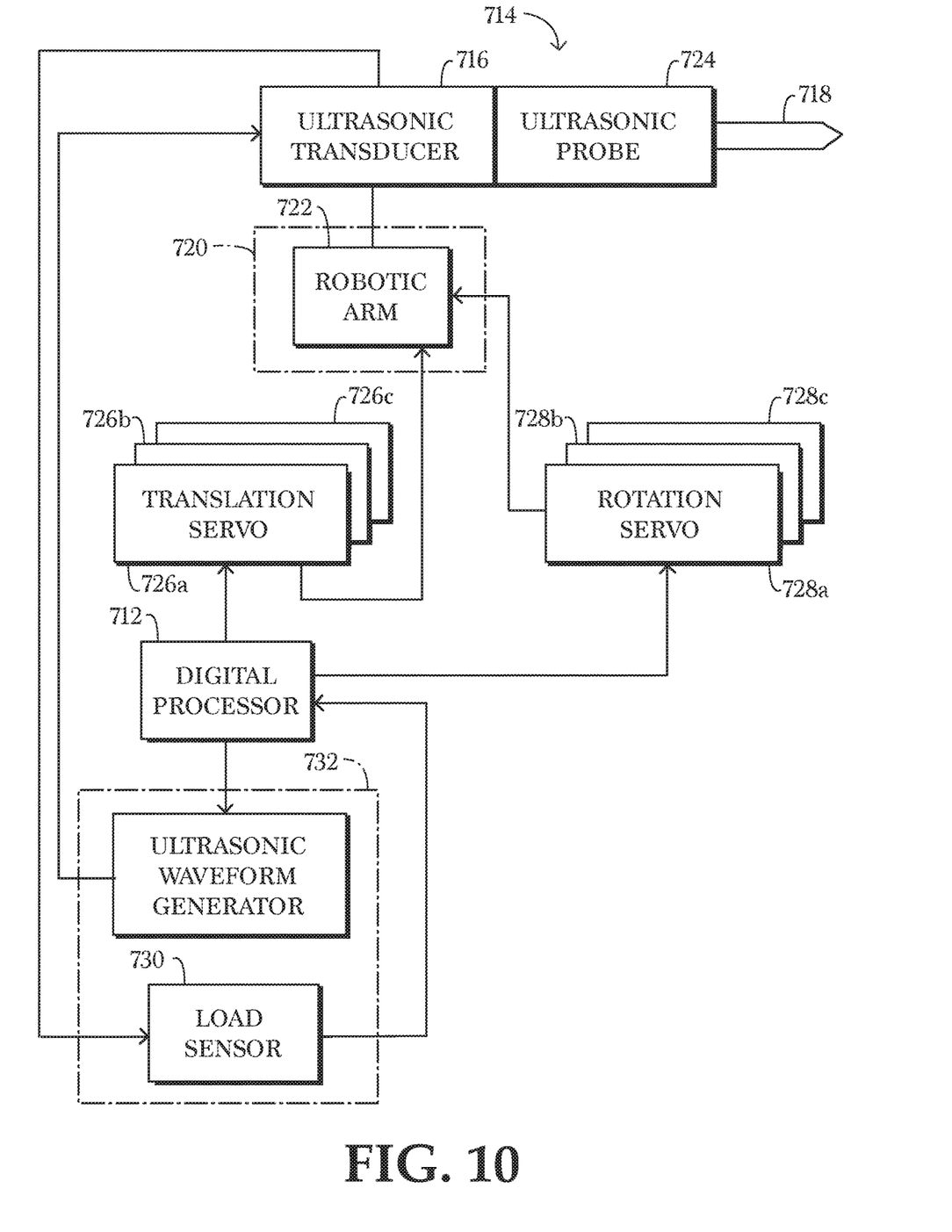
FIG. 10 is a block diagram of a surgical system utilizable in combination with the surgical treatment assembly of FIG. 1, in accordance with the present invention.

FIG. 10 depicts a surgical system utilizable with, and integrated into, the system of FIG. 1, for operation during the distally directed motion of probe 12 under the application of a forward force F, to forestall soft tissue damage on the far or distal side of a bone being drilled or cut. The system of FIG. 1 is therefore used in the transection or drilling of osseous tissue in close proximity to vitally important structures such as the spine. Principal components or subsystems of the system of FIG. 10 include an ultrasonic waveform generator 710 (formed as part of controller 26 in FIG. 1), a digital processor 712 (also part of controller 26), an ultrasonic instrument assembly 714 including an electromechanical transducer 716 (typically the same as transducer 14) and an ultrasonic blade 718 (e.g., head 20 of probe 12), and a robotic system 720. Ultrasonic instrument assembly 714 is attached to a robotic arm 722 of system 720. (Drives 24 and 40 may be component parts of system 720.) Blade 718 is an integral or unitary part of a probe or tool 724 including a shank and a screw connector (neither shown separately) that couples the probe or tool to electromechanical transducer 716 (or 14).

In order to ensure safe operation of the surgical system, there should be no sudden surges in the penetration speed of blade 718 (or probe 12 including head 20) at a breakthrough point, that is, at a point when blade 718 (20) just penetrates through a distal side of a bone being cut. The surgical system of FIG. 10, when incorporated into the system of FIG. 1, is configured so that robotic arm 722 moves ultrasonic blade 718 (or probe 12 with head 20) at a constant forward feed speed through the bone during a cutting operation, that is during a forward or distally directed phase of application of force F (FIG. 1). Digital processor 712 is connected to a plurality of translational servomechanisms 726a, 726b, 726c (equivalent to drive 24 in FIG. 1) and a plurality of rotation servomechanisms 728a, 728b, 728c (equivalent to drive 40 in FIG. 1) that implement degrees of freedom necessary for instrument control. Digital processor 712 reduces forward motion of blade 718 (12, 20) through the bone tissue at a preselected surgical site and preferably halts the forward motion automatically upon a reduction in load per unit time or applied power, as monitored by a pickup or load sensor 730. Alternatively or additionally, power applied to transducer 716 (14, FIG. 1) by waveform generator 710 may be curtailed or interrupted.

Load sensor 730 may be part of a waveform generation subsystem 732, included in effect as part of waveform generator 710. The waveform generation control portion of digital processor 712, as well as the waveform generation subsystem 732 may take a form as described in U.S. Pat. Nos. 8,659,208 and 9,070,856, the disclosures of which are hereby incorporated by reference.

The constant feed speed of blade 718 (probe 12 with head 20, during a positive or distal application of force F in FIG. 1) is maintained by robotic arm 722 in response to the selective activation of servomechanisms 726a, 726b, 726c and 728a, 728b, 728c by digital processor or control unit 712. Load change pickup as detected via load sensor 730 is implemented in a feedback loop of the ultrasonic power application components (digital processor 712, waveform generator 710, transducer 716), more precisely the variation of the drive voltage as a function of load. See U.S. Pat. Nos. 8,659,208 and 9,070,856. In order to maintain a constant motional amplitude, the ultrasonic controls maintain a constant motional current and phase angle while alternatively increasing and decreasing the ultrasonic voltage as a function of rising and falling load. At a breakthrough point, a voltage drop, associated with a decreased load, will be used as input to the servo controls (digital processor 712) for stopping or interrupting the operation of servomechanisms 726a, 726b, 726c and 728a, 728b, 728c. Additionally, the power output of the ultrasonic waveform generator 710 may be at least substantially reduced or interrupted.

Bone cutting blade 718 is formed at a distal end with a cutting edge 734 and may take the form shown in U.S. Pat. Nos. 6,379,371 and 6,443,969. Blade 718 is configured for transmitting ultrasonic vibrational energy, more specifically being dimensioned with probe 724 and transducer 716 to carry therewith an ultrasonic standing wave of desired frequency, exemplarily 22.5 KHz. As discussed above, control unit or processor 712 is operatively connected to robotic arm 722 and configured in part for controlling motion of robotic arm 722 so that the robotic arm moves the bone cutting blade 718 at a constant or uniform rate (speed) through bone tissue during a cutting operation. Electrical or ultrasonic waveform generator 710 is operatively connected to the ultrasonic electromechanical transducer 716 for energizing same to vibrate bone cutting blade 718 at the preselected (design) ultrasonic frequency. Processor 712 is operatively connected to the electrical waveform generator and configured therewith to monitor load on ultrasonic electromechanical transducer 16. Processor 712 is further configured to undertake, upon sensing a reduction in load or applied power (via input from load sensor 730), a control action of inducing the robotic arm 22 to halt motion of bone cutting blade 718 and/or at least substantially reducing waveform energy output of the ultrasonic electromechanical transducer 716.

An associated surgical method utilizing the illustrated surgical system typically includes mounting ultrasonic bone cutting blade 718 and ultrasonic electromechanical transducer 716 to robotic arm 722, and via servomechanisms 726a, 726b, 726c and 728a, 728b, 728c actuating the robotic arm to move the cutting blade at a constant or uniform rate through bone tissue during a surgical cutting operation. Electrical waveform generator 710 is operated to energize electromechanical transducer 716 to vibrate blade 718 at an ultrasonic frequency (e.g., 22.5 kHz) during the surgical cutting operation. The operating of waveform generator 710 includes adjusting power output thereof to maintain a constant vibrational amplitude of the ultrasonic bone cutting blade, as disclosed in U.S. Pat. Nos. 8,659,208 and 9,070,856. The method includes automatically monitoring load or power output of waveform generator 710 and, upon sensing a reduction in load or applied power, operating the servomechanisms 726a, 726b, 726c and 728a, 728b, 728c to actuate robotic arm 722 to halt motion of blade 718 and optionally at least substantially reducing waveform energy output of waveform generator 710.

The operating of the electrical or ultrasonic waveform generator 710 includes adjusting power output thereof to maintain a constant vibrational amplitude of the ultrasonic blade 718. Preferably, this is accomplished by adjusting voltage of the power output of the ultrasonic waveform generator 710 while maintaining motional current and phase angle constant. See U.S. Pat. Nos. 8,659,208 and 9,070,856.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A medical drill assembly comprising:
   a probe connectable at a proximal end to an electromechanical transducer for generating mechanical vibration of an ultrasonic frequency, said probe having a shaft with a central lumen or channel, said shaft being formed at a distal end with an enlarged head having a tapered distal side;
   a source of pressurized liquid communicating with said lumen or channel;
   a translatory or linear drive operatively connected to said probe for applying a distally directed force to said probe;
   a controller operatively connected to said translatory or linear drive for periodically at least reducing the magnitude of said distally directed force; and
   a rotary or oscillating drive operatively connected to said probe for applying a sector rotation to said probe, oscillating said probe about a longitudinal axis thereof through an angle in each angular direction, clockwise and counterclockwise, from a rest position.

2. The medical drill assembly defined in claim 1 wherein said distal side of said head is provided with at least one port or opening communicating with said lumen or channel.

3. The medical drill assembly defined in claim 2 wherein said distal side of said head is formed with a plurality of force-concentrating formations.

4. The medical drill assembly defined in claim 3 wherein said force-concentrating formations are taken from the groups comprising knurls, beads, and teeth.

5. The medical drill assembly defined in claim 3 wherein said distal side of said head is covered throughout with said force-concentrating formations.

6. The medical drill assembly defined in claim 2 wherein said at least one port or opening is centrally located in said distal side of said head.

7. The medical drill assembly defined in claim 2 wherein said at least one port or opening is one of a plurality or ports or openings in said distal side of said head, all of said ports or openings communicating with said lumen or channel.

8. The medical drill assembly defined in claim 1 wherein said controller is operatively connected to said electromechanical transducer for energizing same with an electrical waveform having said ultrasonic frequency and for pulsing said frequency so that the mechanical vibration is periodically interrupted for a predetermined period of time.

9. The medical drill assembly defined in claim 8 wherein the reducing of the magnitude of said distally directed force has a predetermined frequency or periodicity, the pulsing of said frequency has a pulsation frequency or rate that is greater than said predetermined frequency or periodicity.

10. The medical drill assembly defined in claim 1 wherein said rotary or oscillating drive rotates said probe in alternating angular directions about a longitudinal axis of said probe.

11. The medical drill assembly defined in claim 1 wherein said translatory or linear drive is reversible, said controller being operatively connected to said translatory or linear drive to periodically reverse said translatory or linear drive, thereby reducing the magnitude of said distally directed force to zero for intervals of time.

12. The medical drill assembly defined in claim 1 wherein said head has an axially symmetric geometric form.

13. The medical drill assembly defined in claim 1 wherein said head has a geometric shape selected from the group consisting of conical, frusto-conical, convex, and concave.

14. A surgical method comprising:
   providing an ultrasonic probe having a shaft with a central lumen or channel, said shaft being formed at a distal end with an enlarged head having a tapered distal side, said lumen or channel terminating in a port or opening at an outer surface of said head;
   connecting said probe at a proximal end to a source of ultrasonic vibratory energy;
   connecting said lumen or channel to a source of pressurized liquid;
   coupling said probe to a mechanical drive;
   placing said distal side against a surface of a bone;
   while said distal side is in contact with said bone surface, operating said transducer to vibrate said head and said distal side at an ultrasonic frequency;
   while said distal side is in contact with said surface of said bone and while operating said transducer, actuating said drive to exert a force on said probe tending to push said probe into said bone;

while said distal side is in contact with said surface of said bone and while operating said transducer, conducting liquid through said lumen or channel to said port or opening;

while said distal side is in contact with said surface of said bone and while said liquid is being conducted through said lumen or channel to said port or opening, periodically interrupting the actuating of said drive so as to reduce said force; and continuing to operate said transducer to vibrate said head while the actuating of said drive is interrupted.

15. The method defined in claim 14 wherein the periodic interrupting of actuating said drive includes reversing said drive temporarily.

16. The method defined in claim 14 wherein said head is provided with a conical outer surface, said lumen or channel having a plurality branches extending to respective ports or openings in said conical surface, the conducting of liquid through said port or channel including conducting said liquid through said branches to the respective ports or openings.

* * * * *